United States Patent [19]
Mann

[11] Patent Number: 5,385,538
[45] Date of Patent: Jan. 31, 1995

[54] KNEE BRACE HAVING AN INFLATABLE BLADDER SUPPORT

[75] Inventor: Donaerl B. Mann, High Springs, Fla.

[73] Assignee: D'Mannco, Inc., High Springs, Fla.

[21] Appl. No.: 904,844

[22] Filed: Jun. 26, 1992

[51] Int. Cl.⁶ .................................................. A61F 5/00
[52] U.S. Cl. ........................................ 602/26; 602/13; 126/DIG. 20
[58] Field of Search ................. 602/13, 5, 62, 53, 26, 602/23; 128/DIG. 20, 80

[56] References Cited

U.S. PATENT DOCUMENTS

| | | | |
|---|---|---|---|
| 3,548,820 | 12/1970 | Bergen | 602/5 |
| 3,993,056 | 11/1976 | Rabischong et al. | |
| 4,340,042 | 7/1982 | Smith | |
| 4,353,362 | 10/1982 | DeMarco | 602/26 |
| 4,379,463 | 4/1983 | Meier et al. | 602/26 X |
| 4,872,448 | 10/1989 | Johnson, Jr. | |
| 4,938,207 | 7/1990 | Vargo | |
| 4,947,834 | 8/1990 | Kartheus et al. | |
| 4,960,115 | 10/1990 | Ranciato | |

Primary Examiner—Richard J. Apley
Assistant Examiner—Beverly A. Meindl
Attorney, Agent, or Firm—Herbert W. Larson

[57] ABSTRACT

A cloth body having a central knee hole wrapped around a patient's knee to treat knee flexion contractures. Hook and loop straps secure the cloth body to the patient's knee. Longitudinally extending pockets on opposite sides of the knee hole contain a longitudinal support element and an air bladder. Inflation of the air bladder supports the patient's knee in a rigid position.

7 Claims, 3 Drawing Sheets

KNEE BRACE HAVING AN INFLATABLE BLADDER SUPPORT

BACKGROUND OF THE INVENTION

1. Field of the Invention

This invention relates to orthopedic knee brace appliances. More particularly it refers to an orthopedic appliance applied to a patient's knee, the appliance containing an air bladder which is inflated to retain the knee in a rigid configuration.

2. Description of the Prior Art

Many orthopedic appliances exist containing air bladders or fluid control chambers for intermittently supporting and releasing support on body parts. U.S. Pat. No. 3,993,056 describes such appliances having inflatable tubes stitched into a fabric extending vertically over a portion of the fabric. U.S. Pat. No. 4,340,042 describes a pillow type device strapped to a leg and then inflated. U.S. Pat. No. 4,872,448 describes a U-shaped inflatable air bladder over the patella. U.S. Pat. No. 4,938,207 describes a linear brace employing first and second fluid filled chambers. U.S. Pat. No. 4,947,834 describes a brace for compressing patient out extremities, the brace having flexible chambers arranged one after another in a series and these are successively inflated. U.S. Pat. No. 4,960,115 describes a body support apparatus having at least two inflation chambers. None of these appliances provides a means to alternately support a patient's knee in various positions and permit easy removal and reapplication of the splint for treating wounds under the brace. A need exists to have such flexibility in a knee brace support appliance for treating knee flexion contractures and obtain ease of removing and reapplying the brace.

SUMMARY OF THE INVENTION

I have invented a knee brace having an inflatable bladder support to treat knee flexion contractures. My knee brace has a cloth body having a soft bottom portion in contact with the patient's skin and a fabric top surface to which is attached longitudinal pockets, each containing a plastic air bladder and either a rigid support or a hinged support element. Hook and loop straps are also attached to the top surface and a knee hole is centrally located in the cloth body. A hand pump is attached to the bladder to inflate or deflate the bladder as needed by the patient. The wrap around fastening allows for treatment of wounds and incisions by unfastening the hook and loop closures, treating the wound and easily reapplying the brace.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE INVENTION

Figure 1:
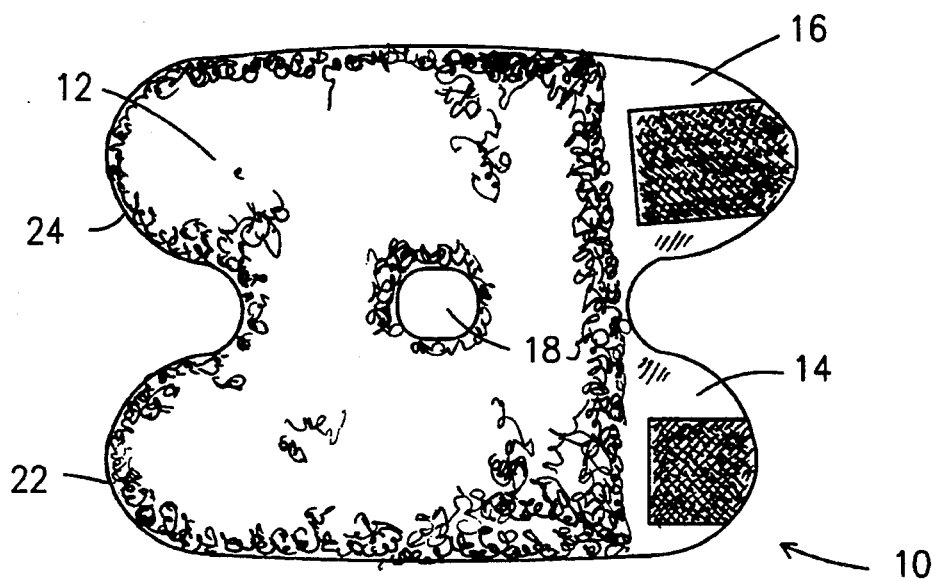
FIG. 1 is a bottom plan view of the orthopedic appliance of my invention prior to applying the appliance to a patient.

Throughout the following detailed description, the same reference numerals refer to the same elements in all figures.

The knee brace 10 is shown in FIG. 1 presenting a bottom plan view thereof. The bottom portion is covered by a pile 12 such as KODEL, a registered trademark for a product sold by Eastman Kodak Company, or other soft wool or wool like material which will not be abrasive to a patient's skin surface. A short section 14 hook and loop material and a longer section 16 projecting from the pile 12 of hook and loop material are used in fastening the brace 10 to a patient's knee. A hole 18 approximately centrally located in the pile material 12 provides an opening for the patient's patella.

Figure 2:
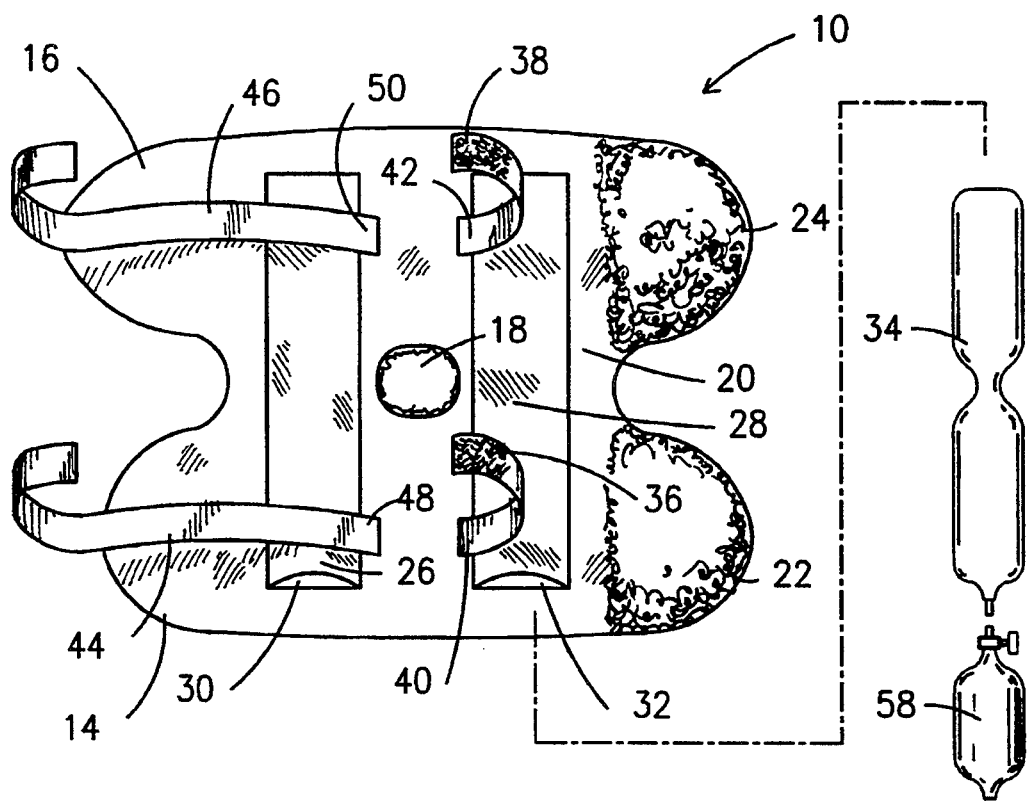
FIG. 2 is a top plan view of the orthopedic appliance shown in FIG. 1.

FIG. 2 shows a top plan view of the knee brace 10. The top surface of the brace is covered by tightly woven fabric 20. Projecting sections of hook and loop material 22 and 24 are attached by sewing to the tightly woven fabric 20. The bottom portions of hook and loop material 22 and 24 are covered by The pile 12. Also shown in FIG. 2 is a pair of pockets 26 and 28 respectively sewn to the top surface of the fabric 20. An opening 30 to pocket 26 and an opening 32 to pocket 28 provides a means for inserting an air bladder 34 into each pocket. Straps 40 and 42 are also sewn on to the fabric 20 with the bottom surface 36 and 38 respectively of straps 40 and 42 covered with hook and loop material. The top surface 44 and 46 respectively of straps 48 and 50 are covered by hook and loop material. The reverse side of each strap 44 and 46 has a cloth material. The top surface of pad sections 14 and 16 are covered by fabric material. In addition to the bladder 34 either a hinge support element 52 or a rigid support element 54 as shown respectively in FIGS. 4 and 5 are inserted in the pocket 32.

Figures 3, 4, 5, 6:
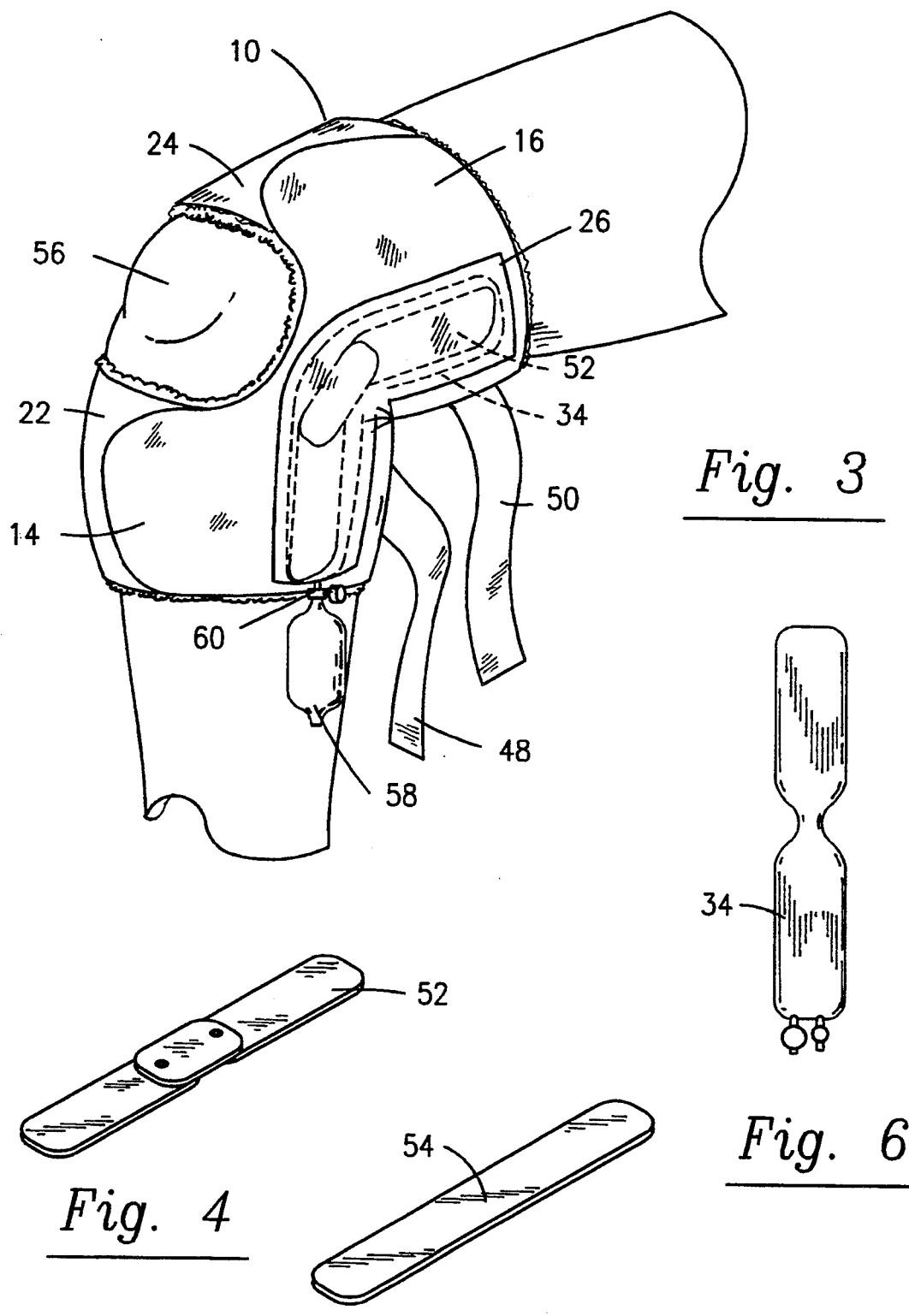
FIG. 3 is a perspective view of the orthopedic appliance positioned on a patient's knee with the air bladder and hinged support elements shown in phantom.
FIG. 4 is a perspective view of the hinged support element.
FIG. 5 is a perspective view of the rigid support element.
FIG. 6 is a top plan view of the air bladder mounted within a pocket.

FIG. 3 shows the splint 10 mounted over the knee 56 of a patient. Flap 16 is folded over on to flap 24 so that the hook and loop material on the bottom of flap 16 engages the hook and loop material on the top of flap 24. In like manner the flap 14 is passed over flap 22 so that the hook and loop material on the bottom portion of flap 14 engages the corresponding hook and loop material on the top portion of flap 22. In the brace 10 shown in FIG. 3 a hinged support element 52 is employed in the pocket 26 with bladder 34 so that the patient can bend his leg. A bulb pump 58 is attached by its valve 60 to the corresponding valve opening in bladder 34 to enable the bladder to be expanded and rigidly support the patient's knee in the designated position.

Figure 7:
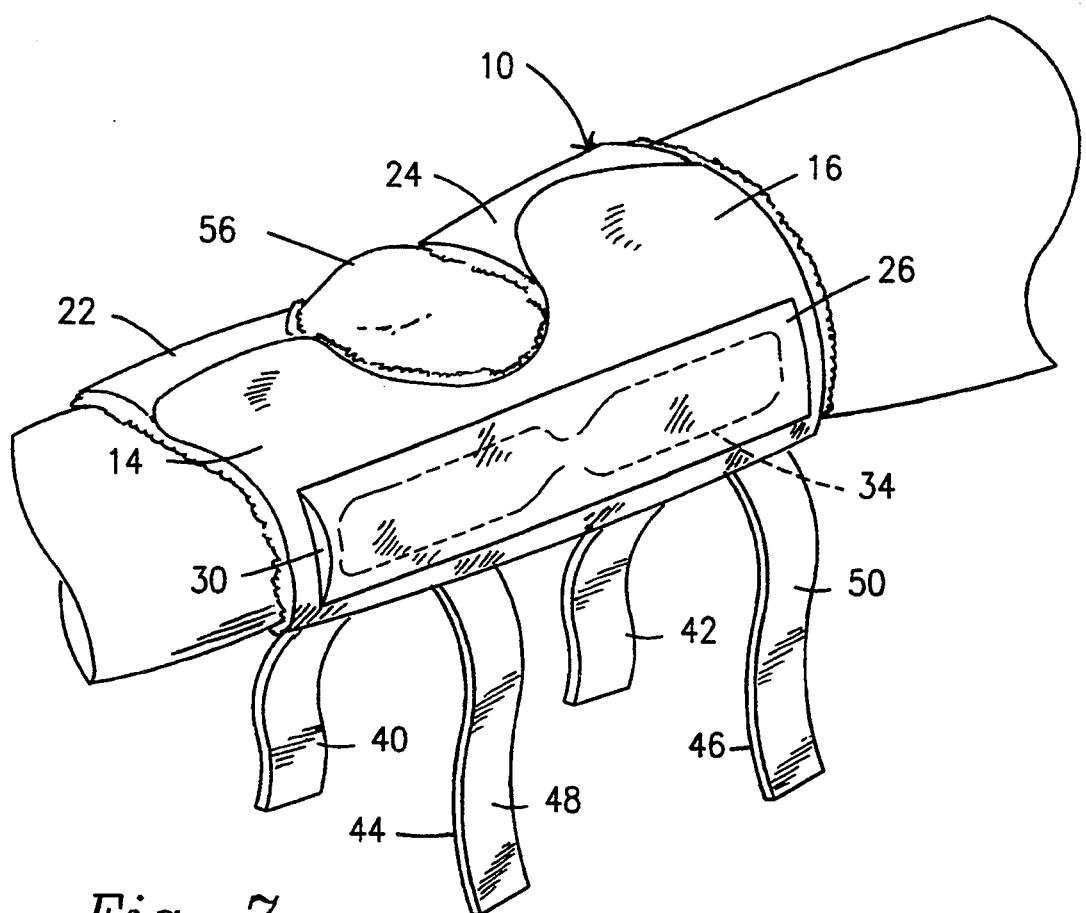
FIG. 7 is a perspective view of the orthopedic appliance draped over a patient's knee.
Figure 8:
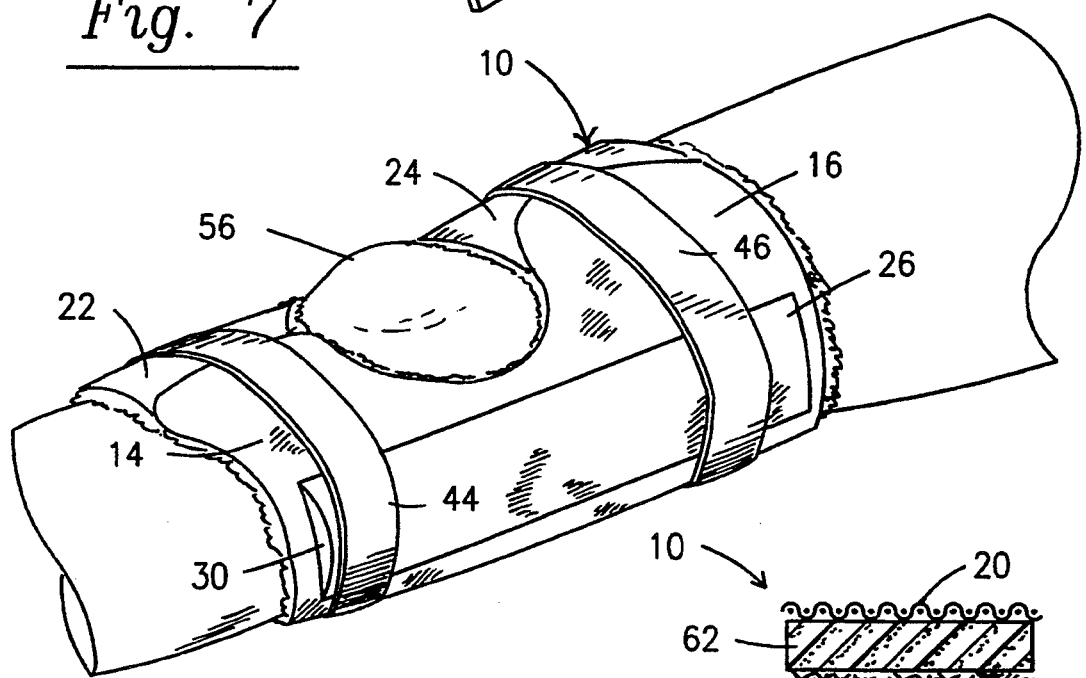
FIG. 8 is a perspective view of the orthopedic appliance retaining a patient's knee in a fixed position.

As shown in FIG. 7 a rigid support element 54 can be employed in pocket 26 together with a bladder 34 to maintain a completely rigid configuration for the patient's leg. Straps 48 and 50 respectively are attached to corresponding hook and loop material 36 and 38 on straps 40 and 42 respectively by wrapping around the patient's leg. This produces the configuration shown in FIG. 8 where the patient's leg is extended in a fixed position with the bladder 34 filled to maintain the leg in a fixed position.

Figure 9:
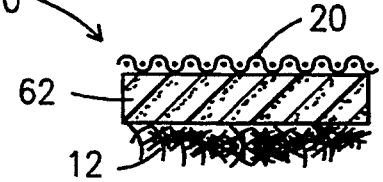
FIG. 9 is a cross sectional view through the cloth body of the orthopedic appliance.

As shown in FIG. 9 the fabric surface 20 is separated from the pile surface 12 by an intermediate foam layer 62 so that the brace 10 has a soft wool-like material 12 in contact with the skin and a durable fabric 20 on the outside protecting the brace from environmental effects but with a foam intermediate material to maintain the body structure of the splint while at the same time providing a soft medium to prevent pressure against the soft tissue of the leg.

The knee brace 10 of this invention is designed primarily treat pre-fixed contracture of the knee. Such pre-fixed contracture is any contracted joint that can be flexed or extended and where splinting is indicated for treatment. The brace 10 will stabilize the extension of the knee and is useful for immobilization of the knee post-trauma or post-surgery. In addition the brace 10 will support post-trauma or surgery patients while undergoing rehabilitation.

In placing the brace 10 on a patient the leg is extended as far as comfort will allow and the open brace 10 is place on the patient's knee with the extension 16 placed around the thigh to contact the extension 24 on the fabric. The pile surface 12 is placed down over the patient's skin. The air bladder is inflated to hold the leg in the degree of extension desired. The greater the degree of extension, the more inflation in the air bladder 34. If the patient is ambulating the hinged support element 52 is used in the pockets 26 and 38 whereas if the knee should be completely immobilized the rigid support element 54 is inserted in pockets 26 and 28. After the correct air pressure is reached the pile straps 48 and 50 are connected to straps 40 and 42 respectively. Once the amount of air pressure necessary for either stabilization or immobilization has been determined the splint can be removed and put back on without changing the air pressure in the air bladder 34. To remove the brace the straps are all unfastened. To replace the splint extend the leg and place the splint pile side toward the leg under the leg and fasten the wide straps over and under the knee. Then fasten the remaining straps over and under the knee. One finger should be inserted under all edges for correct clearance. The splint 10 can be easily removed and replaced in order to treat wounds under the splinted area.

Equivalent materials can be substituted for the materials employed in this invention to obtain substantially the same result in the same way.

Having thus described the invention, what is claimed and desired to be secured by Letters and Patent is:

1. An orthotic appliance to treat knee flexion contractures comprising a cloth body for wrapping around a patient's knee having a generally centrally located hole for a dorsal surface of the knee to protrude through the cloth body, the cloth body having a soft bottom layer in contact with the patient, a tightly woven fabric top layer and a soft foam layer intermediate the bottom and top layers, hook and loop securing straps attached to the top layer to provide a means to maintain the cloth body in position wrapped around the patient's knee, a pair of longitudinal pockets integral with the cloth body top layer on opposite sides of the hole, a longitudinal support element mounted within each pocket, and an air bladder mounted adjacent the longitudinal support element in each pocket being capable of inflation to rigidly support the patient's knee and deflation to allow the patient to move the knee.

2. An orthotic appliance according to claim 1 wherein the soft bottom layer of the cloth body is a synthetic wool like pile.

3. An orthotic appliance according to claim 1 wherein the longitudinal support element is hinged to permit movement of a patient's leg.

4. An orthotic appliance according to claim 1 wherein the longitudinal support element is a rigid flat plastic member which restricts movement of a patient's leg.

5. An orthotic appliance according to claim 1 wherein the air bladder is hour glass in shape.

6. An orthotic appliance according to claim 1 wherein the air bladder is a soft plastic body.

7. An orthotic appliance according to claim 1 wherein the air bladder contains a valve to permit both ingress and egress of air.

* * * * *